United States Patent
Cai et al.

(10) Patent No.: US 11,155,900 B2
(45) Date of Patent: Oct. 26, 2021

(54) NICKEL-TITANIUM-YTTRIUM ALLOYS WITH REDUCED OXIDE INCLUSIONS

(71) Applicant: Fort Wayne Metals Research Products Corp, Fort Wayne, IN (US)

(72) Inventors: Song Cai, Fort Wayne, IN (US); Jeremy E. Schaffer, Fort Wayne, IN (US); Adam J. Griebel, Fort Wayne, IN (US)

(73) Assignee: Fort Wayne Metals Research Products Corp., Fort Wayne, IN (US)

( * ) Notice: Subject to any disclaimer, the term of this patent is extended or adjusted under 35 U.S.C. 154(b) by 291 days.

(21) Appl. No.: 16/095,149

(22) PCT Filed: Apr. 19, 2017

(86) PCT No.: PCT/US2017/028388
§ 371 (c)(1),
(2) Date: Oct. 19, 2018

(87) PCT Pub. No.: WO2017/184750
PCT Pub. Date: Oct. 26, 2017

(65) Prior Publication Data
US 2020/0354816 A1 Nov. 12, 2020

Related U.S. Application Data

(60) Provisional application No. 62/325,283, filed on Apr. 20, 2016.

(51) Int. Cl.
*C22C 19/03* (2006.01)
*C21D 8/02* (2006.01)
(Continued)

(52) U.S. Cl.
CPC .............. *C22C 19/03* (2013.01); *C21D 8/02* (2013.01); *C21D 8/06* (2013.01); *C21D 9/08* (2013.01); *C21D 9/46* (2013.01); *C21D 9/525* (2013.01)

(58) Field of Classification Search
CPC .. C22C 19/03; C21D 8/02; C21D 8/06; C21D 9/08; C21D 9/46; C21D 9/525
See application file for complete search history.

(56) References Cited

U.S. PATENT DOCUMENTS 8,152,941 B2   4/2012   Sczerzenie et al.
8,398,789 B2   3/2013   Wong et al.
(Continued)

FOREIGN PATENT DOCUMENTS

CN    103906850    7/2014
EP    2768993      8/2014
(Continued)

OTHER PUBLICATIONS

Miller et al. ("Influence of cold work and heat treatment on the shape memory effect and plastic strain development of NiTi." Materials Science and Engineering: A 308.1-2 (2001): 161-175.) (Year: 2001).*

(Continued)

*Primary Examiner* — Anthony J Zimmer
*Assistant Examiner* — Ricardo D Morales
(74) *Attorney, Agent, or Firm* — Faegre Drinker Biddle & Reath LLP

(57) ABSTRACT

A nickel-titanium alloy is made to be wholly or substantially free of titanium-rich oxide inclusions by including yttrium in an amount up to 0.15 wt. %, with the balance of the alloy being nickel and titanium in approximately equal proportion. For example, a NiTiY alloy may have a composition including, in weight percent based on total alloy weight:

(Continued)

between 50 and 60 wt. % nickel; between 40 and 50 wt. % titanium; and between 0.01 and 0.15 wt. % yttrium. The resulting alloy is capable of being drawn into various forms, e.g., fine medical-grade wire, without exhibiting an unacceptable tendency to develop surface defects or to fracture or crack during cold drawing or forging. The resulting final forms exhibit favorable fatigue strength and fatigue-resistant characteristics.

15 Claims, 8 Drawing Sheets

(51) Int. Cl.
*C21D 8/06* (2006.01)
*C21D 9/08* (2006.01)
*C21D 9/46* (2006.01)
*C21D 9/52* (2006.01)

(56) References Cited

U.S. PATENT DOCUMENTS

| | | | |
|---|---|---|---|
| 8,440,031 B2 | 5/2013 | Syed et al. | |
| 8,840,735 B2 * | 9/2014 | Schaffer | A61L 31/14 148/325 |
| 9,074,274 B2 | 7/2015 | Tofail et al. | |
| 10,000,827 B2 | 6/2018 | Tofail et al. | |
| 2007/0073374 A1 | 3/2007 | Anderl et al. | |
| 2009/0248130 A1 | 10/2009 | Boylan | |
| 2011/0277568 A1 | 11/2011 | Sczerzenie et al. | |
| 2011/0319978 A1 | 12/2011 | Schaffer | |
| 2012/0189486 A1 | 7/2012 | Sczerzenie et al. | |
| 2013/0101455 A1 | 4/2013 | Tofail et al. | |
| 2013/0183188 A1 | 7/2013 | Tofail et al. | |
| 2013/0205567 A1 | 8/2013 | Wong et al. | |
| 2014/0257451 A1 | 9/2014 | Simpson et al. | |
| 2015/0315681 A1 | 11/2015 | Munroe et al. | |

FOREIGN PATENT DOCUMENTS

| | | | | |
|---|---|---|---|---|
| EP | 2804711 | | 11/2014 | |
| JP | 48-038531 A | | 6/1973 | |
| JP | 48-038532 A | | 6/1973 | |
| JP | 60-251241 A | | 12/1985 | |
| JP | 60251241 A | * | 12/1985 | |
| JP | 61-210142 A | | 9/1986 | |
| JP | 08-060277 A | | 3/1996 | |
| JP | H080277 A | * | 3/1996 | ............. C22C 19/03 |
| JP | 2013-508556 A | | 3/2013 | |
| JP | 2014534342 | | 12/2014 | |
| JP | 2015510036 | | 4/2015 | |
| RU | 2100468 C1 | | 12/1997 | |
| UA | 94009 C2 | * | 1/2011 | ............. C22C 19/03 |
| UA | 94009 C2 | | 3/2011 | |
| WO | 2005/045087 A1 | | 5/2005 | |
| WO | 2013057292 | | 4/2013 | |
| WO | 2013109846 | | 7/2013 | |

OTHER PUBLICATIONS

Mitsuru et al. (JPH080277A) espacenet translation (Year: 1996).*
JP-60251241-A English translation (Year: 1985).*
International Search Report and Written Opinion dated Jul. 19, 2017 in PCT/US2017/028388.
International Preliminary Report on Patentability received for PCT Patent Application No. PCT/US2017/028388, dated Nov. 1, 2018, 8 pages.
Extended European search report includes Supplementary European search report received for EP Application No. 17786567.2, dated Nov. 14, 2019, 8 pages.
Office Action received for Chinese Patent Application No. 201780037850.0, dated Apr. 17, 2020, 20 pages (9 pages of English Translation and 11 pages of Original Document).

* cited by examiner

NICKEL-TITANIUM-YTTRIUM ALLOYS WITH REDUCED OXIDE INCLUSIONS

CROSS REFERENCE TO RELATED APPLICATIONS

This present application is a national phase filing under 35 U.S.C. § 371 of International Application No. PCT/US2017/028388, entitled "NICKEL-TITANIUM-YTTRIUM ALLOYS WITH REDUCED OXIDE INCLUSIONS," filed on Apr. 19, 2017, which claims the benefit under Title 35, U.S.C. § 119(e) of U.S. Provisional Patent Application Ser. No. 62/325,283, entitled NICKEL-TITANIUM-YTTRIUM ALLOYS WITH REDUCED OXIDE INCLUSIONS and filed on Apr. 20, 2016, the entire disclosures of which are hereby expressly incorporated by reference herein.

BACKGROUND

1. Technical Field

The present disclosure is directed to shape-memory alloys and methods of making the same, and in particular, to nickel-titanium shape-memory alloys with enhanced fatigue performance.

2. Description of the Related Art

Specialized alloys have been developed for surgical implant applications. One such alloy, known as Nitinol (also commonly referred to as "NiTi"), is produced in bar and wire forms intended for use in surgical implants such as, for example, stents and pacing leads adapted to relay a cardiac pacing pulse from an implanted defibrillator or pacing device to the heart. NiTi and similar ternary, quaternary, and quinary alloys are also envisioned for use as actuators, or solid state thermal motors that can be used to replace motors for axial, flexural, or rotary motion in automotive, aerospace and medical devices and machines.

Standard specifications and chemistry for wrought NiTi alloy for use in surgical implant applications may be found in ASTM F2063, the entire disclosure of which is hereby incorporated herein by reference. A material constituency for materials made in accordance with ASTM F2063 is shown below as Table 1.

TABLE 1

Chemical Composition Requirements

| Element | % (mass/mass) |
|---|---|
| Nickel | 54.5 to 57.0 |
| Carbon, maximum | 0.050 |
| Cobalt, maximum | 0.050 |
| Copper, maximum | 0.010 |
| Chromium, maximum | 0.010 |
| Hydrogen, maximum | 0.005 |
| Iron, maximum | 0.050 |
| Niobium, maximum | 0.025 |
| Nitrogen plus Oxygen, maximum | 0.050 |
| Titanium[A] | Balance |

[A]Approximately equal to the difference between 100% and the sum percentage of the other specified elements. The percentage titanium content by difference is not required to be reported.

In some cases, the fatigue performance of NiTi alloys may be limited by inclusions (shown in FIG. 1A, which are drawn to scale according to scale 9) such as oxides and carbides which are formed during melting and solidification. Carbides are relatively small in size, and are generally formed due to carbon contamination from the graphite crucible used in the Vacuum Induction Melt (VIM). By contrast, oxides are normally substantially larger than carbides in the as-cast condition. Oxides may break up during processing (e.g., during hot forming or cold forming processes) to form stringers. FIG. 1A shows the microstructure of an ingot 1 formed of a binary NiTi alloy at a magnification such that the illustrated scale in the lower-right hand corner of the image corresponds to 20 μm. As shown in the image of FIG. 1A, inclusions 5 are formed within the microstructure 3 of the alloy, and may contribute to the formation of stringers when the alloy is processed.

Known methods for reducing the fraction of the oxide include using higher purity raw material, zone refinement, high-energy re-melting such as plasma or electron beam methods, and using a high vacuum (i.e. greater multiples lower than atmospheric pressure) during ingot melting and solidification. Methods that employ combinations of high purity raw metals and/or high energy melting, including high-vacuum methods, are expensive and not practically attractive due to high energy consumption and associated high production costs. Other oxide-reduction methods such as those described above also involve high input costs and/or low process yields.

What is needed is an improvement over the foregoing.

SUMMARY

The present disclosure is directed to a nickel-titanium alloy made to be wholly or substantially free of titanium-rich oxide inclusions by including yttrium in an amount up to 0.15 wt. %, with the balance of the alloy being nickel and titanium in approximately equal proportion. For example, a NiTiY alloy may have a composition including, in weight percent based on total alloy weight: between 50 wt. % and 60 wt. % nickel; between 0.01 and 0.15 wt. % yttrium; and balance titanium. The resulting alloy is capable of being drawn into various forms, e.g., fine medical-grade wire, without exhibiting an unacceptable tendency to develop surface defects or to fracture or crack during cold drawing or forging. The resulting final forms exhibit favorable fatigue strength and fatigue-resistant characteristics.

The present disclosure is further directed to articles of manufacture including any of the novel alloys described herein. Examples of such articles of manufacture include a bar, a wire, a tube, a surgical implant device, a component for a surgical implant device, an implantable defibrillator, a component for an implantable defibrillator, an implantable pace maker, a component for an implantable pacemaker, a pacing lead, and a vascular or non-vascular stent. In instances where the article of manufacture is a bar or a wire, the article also may be one qualified for use in surgical implant applications under ASTM standard specification F2063.

The present disclosure is additionally directed to a method of making an alloy, wherein the method includes preparing an ingot having the chemistry set forth above. In certain embodiments of the method, the ingot is wholly or substantially free of carbide and titanium-rich oxide inclusions. The method may also include processing the ingot into one of a bar, a wire, and a tube, which may be further processed into an article of manufacture as described herein.

In one form thereof, the present disclosure provides a nickel-titanium (NiTi) alloy, comprising: between 50 wt. % nickel and 60 wt. % nickel; between 40 wt. % titanium and 50 wt. % titanium; and between 0.01 wt. % yttrium and 0.15 wt. % yttrium.

In another form thereof, the present disclosure provides a nickel-titanium (NiTi) alloy, comprising: at least 20 wt. % nickel; between 35 wt. % titanium and 55 wt. % titanium; between 0.01 wt. % yttrium and 0.15 wt. % yttrium; and at least one of: copper between 1 wt. % and 10 wt. %, in lieu of an equal amount of nickel; niobium between 1 wt. % and 15 wt. %, in lieu of an equal amount of titanium; hafnium between 0.5 wt. % and 50 wt. %, in lieu of an equal amount of titanium; zirconium between 0.5 wt. % and 35 wt. %, in lieu of an equal amount of titanium; cobalt between 0.1 wt. % and 5 wt. %, in lieu of an equal amount of titanium, nickel, or a combination of titanium and nickel; chromium between 0.1 wt. % and 1 wt. %, in lieu of an equal amount of titanium; and iron between 0.1 wt. % and 10 wt. %, in lieu of an equal amount of titanium, nickel, or a combination of titanium and nickel.

In yet another form thereof, the present disclosure provides a method of making a nickel-titanium (NiTi) alloy, comprising: providing between 50 wt. % nickel and 60 wt. % nickel; providing between 40 wt. % titanium and 50 wt. % titanium; providing between 0.01 wt. % yttrium and 0.15 wt. % yttrium; and forming an ingot including the nickel, the titanium and the yttrium.

In still another form thereof, the present disclosure provides a method of making a nickel-titanium (NiTi) alloy, comprising: providing at least 20 wt. % nickel; providing between 35 wt. % titanium and 55 wt. % titanium; providing between 0.01 wt. % yttrium and 0.15 wt. % yttrium; providing at least one of an additional element; and forming an ingot including the nickel, the titanium and the yttrium, the ingot further including at least one of the copper, the niobium, the hafnium, the zirconium, the cobalt, the chromium and the iron. The additional elements may be any of the following: copper between 1 wt. % and 10 wt. %, in lieu of an equal amount of nickel; niobium between 1 wt. % and 15 wt. %, in lieu of an equal amount of titanium; hafnium between 0.5 wt. % and 50 wt. %, in lieu of an equal amount of titanium; zirconium between 0.5 wt. % and 35 wt. %, in lieu of an equal amount of titanium; cobalt between 0.1 wt. % and 5 wt. %, in lieu of an equal amount of titanium, nickel, or a combination of titanium and nickel; chromium between 0.1 wt. % and 1 wt. %, in lieu of an equal amount of titanium; and iron between 0.1 wt. % and 10 wt. %, in lieu of an equal amount of titanium, nickel, or a combination of titanium and nickel.

BRIEF DESCRIPTION OF THE DRAWINGS

The above mentioned and other features and objects of this invention, and the manner of attaining them, will become more apparent and the invention itself will be better understood by reference to the following description of embodiments of the invention taken in conjunction with the accompanying drawings, wherein.

Figure 1A:
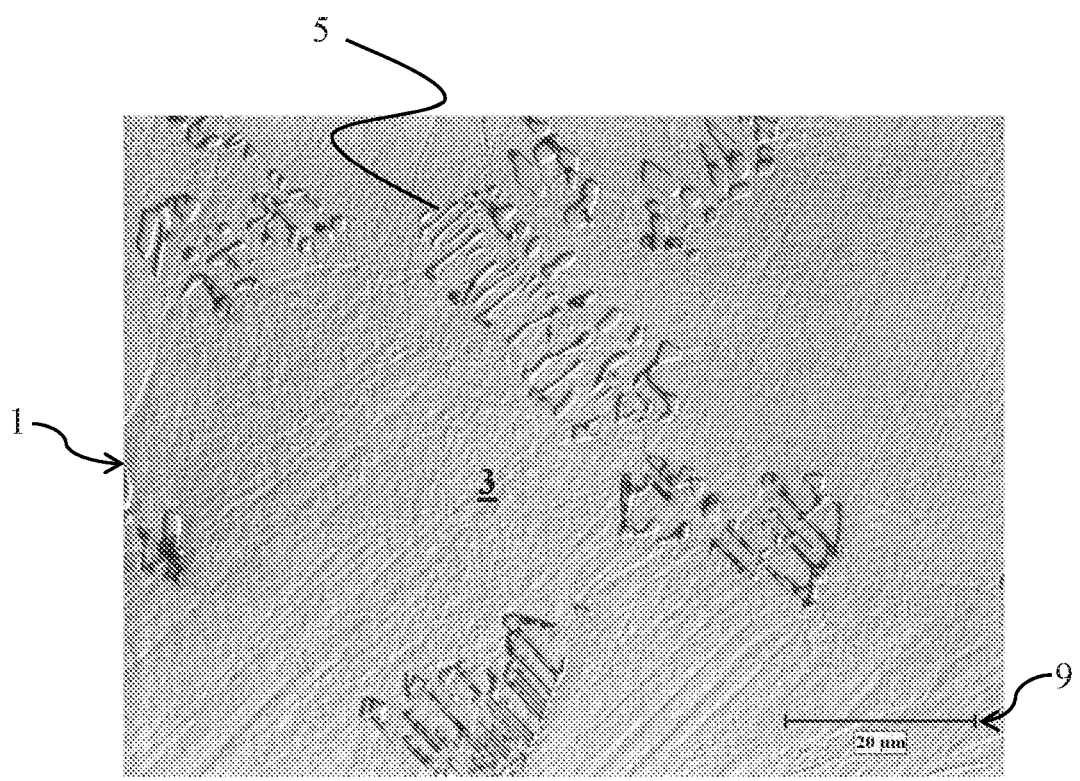
FIG. 1A is an image of an ingot of a known NiTi alloy in an as-cast condition, in which the ingot and its associated microstructural features are shown to scale according to the illustrated scale in micrometers in the bottom right hand corner of the figure.

Corresponding reference characters indicate corresponding parts throughout the several views. Although the exemplifications set out herein illustrate embodiments of the invention, the embodiments disclosed below are not intended to be exhaustive or to be construed as limiting the scope of the invention to the precise form disclosed.

DETAILED DESCRIPTION

Introduction

The alloy of the present disclosure is a nickel-titanium-yttrium (NiTiY) alloy that, in certain embodiments, exhibits significantly improved properties depending on the specific concentration of yttrium present in the alloy. For example, the present NiTiY alloys having only a small (e.g., less than 0.15 wt. %) amount of yttrium exhibit improved fatigue resistance relative to conventional NiTi alloys and benefit from a significantly lower fracture rate compared to conventional NiTi alloys, particularly when the alloy is in the form of a fine drawn wire with a small diameter as may be desired for use in pacing leads and certain other surgical implant applications.

Terminology

As used herein, "wire" or "wire product" encompasses continuous wire and wire products which may be continuously produced and wound onto a spool for later dispensation and use, such as wire having a round cross section and wire having a non-round cross section, including flat wire or ribbon. "Wire" or "wire product" also encompasses other wire-based products such as strands, cables, coil, and tubing, which may be produced at a particular length depending on a particular application. In some exemplary embodiments, a wire or wire product in accordance with the present disclosure may have a diameter up to 2.5 mm. In addition to wire and wire products, the principles of the present disclosure can be used to manufacture other material forms such as rod materials having a diameter greater than 2.5 mm up to 20 mm. Thin material sheets may also be made. Exemplary tubing structures may be in wire form or rod form, with inside diameters ranging from 0.5 mm to 4.0 mm, and wall thicknesses ranging from 0.100 mm to 1.00 mm. "Fine wire" refers to a wire having an outer diameter of less than 1 mm.

As used herein, "fatigue strength" refers to the load level at which the material meets or exceeds a given number of load cycles to failure. Herein, the load level is given as alternating strain, as is standard for displacement or strain-controlled fatigue testing, whereby terms are in agreement with those given in ASTM E606, the entirety of which is incorporated herein by reference.

"Nitinol" is a trade name for a shape memory alloy comprising approximately 50 atomic % Nickel and balance Titanium, also known as NiTi, commonly used in the medical device industry for highly elastic metallic implants.

"Superelastic" material is material which is capable of undergoing strain exceeding 2% with negligible plastic deformation, such that the material is able to return to its original dimension after the deformation without permanent damage.

"DFT®" is a registered trademark of Fort Wayne Metals Research Products Corp. of Fort Wayne, Ind., and refers to a bimetal or poly-metal composite wire product including two or more concentric layers of metals or alloys, typically at least one outer layer disposed over a core filament formed by drawing a tube or multiple tube layers over a solid metallic wire core element.

"NiTi oxides," in the context of binary NiTi alloys, are $Ti_XNi_YO_Z$ particles that form from $Ti_XNi_Y$ intermetallics with an oxygen content of as much as 15 at %. Oxygen may be present in raw materials used for NiTi creation, or may be drawn from the atmosphere during melting and ingot formation. Although the total amount of oxygen in the alloy is very small (e.g. ~200 ppm) in most cases, the present inventors recognize that oxygen does not dissolve in the NiTi binary alloy, and so becomes part of intermetallic $Ti_XNi_Y$ during solidification and stabilizes in the form of $Ti_XNi_YO_Z$ oxide particles. These stabilized NiTi oxides cannot be dissolved by homogenization and unavoidably exist in Ti-rich, Ni-Rich and substantially equiatomic, or equal atomic proportion, binary NiTi alloys. Ternary NiTi alloys, such as TiNiCu and TiNiNb, may also form oxides taking the form of, e.g., $Ti_X(Cu,Ni)_YO_Z$ or $(Ti,Nb)_XNi_YO_Z$, it being understood that these and other ternary oxides may be within the scope of "NiTi oxides" as used herein.

"Impurities," "incidental impurities" and "trace impurities" are material constituents present in a material at less than 500 parts per million or 0.05 wt. % for any given element, except that yttrium is not considered an impurity within the context of the present disclosure.

Yttrium Alloyed with Nickel and Titanium

As noted above with respect to FIG. 1A (which is drawn to scale, according to scale 9), oxide inclusions may form within the microstructure of ingot 1. With the recognition that such inclusions may potentially adversely affect fatigue life of traditional binary NiTi alloys, materials made in accordance with the present disclosure were produced and tested to present a solution to such variability and/or enhance the mechanical properties of the material. Specific examples of such materials are described below in the Working Examples.

Surprisingly, including only a small amount of yttrium to form an alloy of nickel-titanium-yttrium (NiTiY) has been found to reduce the number of oxide inclusions present in the alloy during melting and solidification, without the use of expensive traditional methods for reducing the amount of oxygen present in and around the alloy. As noted above, two such expensive traditional methods include using extremely high purity raw material, e.g., 99.9995% pure nickel and 99.9995% pure titanium, and forming the NiTi alloy in an extremely high atmospheric vacuum, e.g., in a pressure below $10^{-2}$ Pa (0.07 mTorr).

By contrast and as further described in detail below and in the Working Examples, the present class of NiTiY alloys are at least as effective as these expensive alternatives, with the use of 99.95% pure nickel, 99.8% pure titanium and a vacuum pressure of about 0.67 Pa (5 mTorr).

Embodiments of the nickel-titanium-yttrium alloy of the present disclosure have a chemistry that differs from the conventional chemistry of NiTi alloy. These chemical differences provide an alloy that, although meeting the broad chemistry requirements for medical-grade NiTi alloy under ASTM F2063, further includes an amount of yttrium that is not present in a conventional NiTi alloy. The differences in chemistry in the modified NiTiY alloys to which the present disclosure is directed have been found to inhibit the formation of undesirable oxide inclusions in the alloys. This, in turn, improves the ability to process the alloy to bar and wire form and enhances the fatigue resistance of alloy and products produced from the alloy.

Moreover, improvements in performance and character of the NiTiY alloys described herein have been observed, corresponding to the significant reduction or elimination of the presence of $Ti_XNi_YO_Z$ oxide inclusions in the alloys. The properties of the alloy vary depending on the concentration of yttrium in the alloy.

In addition, carbide inclusions (described above) may be limited in the present alloy materials by using "cold wall"

methods that do not use a graphite crucible, such as Vacuum Arc Re-melt (VAR), Induction Skull Melt (ISM) or by using levitation melt that uses a water-cooled copper crucible.

The yttrium concentration in the present NiTiY alloy may be as little as 0.01 wt. %, 0.02 wt. % or 0.03 wt. %, and as much as 0.08 wt. %., 0.12 wt. % or 0.15 wt. %., or may be any concentration in any range defined by any of the foregoing values. For example, the yttrium concentration in the present NiTiY alloy may be:

between 0.01 wt. % and 0.02 wt. % yttrium;
between 0.01 wt. % and 0.03 wt. % yttrium;
between 0.01 wt. % and 0.08 wt. % yttrium;
between 0.01 wt. % and 0.12 wt. % yttrium;
between 0.01 wt. % and 0.15 wt. % yttrium;
between 0.02 wt. % and 0.03 wt. % yttrium;
between 0.02 wt. % and 0.08 wt. % yttrium;
between 0.02 wt. % and 0.12 wt. % yttrium;
between 0.02 wt. % and 0.15 wt. % yttrium;
between 0.03 wt. % and 0.08 wt. % yttrium;
between 0.03 wt. % and 0.12 wt. % yttrium;
between 0.03 wt. % and 0.15 wt. % yttrium;
between 0.08 wt. % and 0.12 wt. % yttrium;
between 0.08 wt. % and 0.15 wt. % yttrium; or
between 0.12 wt. % and 0.15 wt. % yttrium.

Moreover, the amount of yttrium used in the present NiTiY alloy may also be a function of expected or actual oxygen impurities for feedstock materials, with lower Y concentrations being sufficient for relatively more pure Ni and Ti feedstock materials, and higher concentrations needed for relatively less pure Ni and Ti feedstock materials.

In the ternary NiTiY alloy described above, the amounts of nickel and titanium are roughly equal and form the balance of the alloy. The nickel concentration in the present NiTiY alloy may be as little as 50 wt. %, 52 wt. % or 54.5 wt. %, and as much as 57 wt. %., 58.5 wt. % or 60 wt. %., or may be any concentration in any range defined by any of the foregoing values. For example, the nickel concentration in the present NiTiY alloy may be:

between 50 wt. % and 52 wt. %;
between 50 wt. % and 54.5 wt. %;
between 50 wt. % and 57 wt. %;
between 50 wt. % and 58.5 wt. %;
between 50 wt. % and 60 wt. %;
between 52 wt. % and 54.5 wt. %;
between 52 wt. % and 57 wt. %;
between 52 wt. % and 58.5 wt. %;
between 52 wt. % and 60 wt. %;
between 54.5 wt. % and 57 wt. %;
between 54.5 wt. % and 58.5 wt. %;
between 54.5 wt. % and 60 wt. %;
between 57 wt. % and 58.5 wt. %;
between 57 wt. % and 60 wt. %; or
between 58.5 wt. % and 60 wt. %.

Titanium may then form the balance of the alloy. Therefore, titanium may be any constituency between 39.85 wt. % and 49.99 wt. %, and may form the balance of any alloy formed from any of the foregoing ranges of Ni and Y.

In addition, the present NiTiY material may be further alloyed with other materials as required or desired for various potential applications. Examples of further alloying elements within the scope of the present disclosure include the following elements in the following amounts in any combination or permutation, provided, however, that nickel can only be displaced by the following element(s) to the extent that a minimum nickel content of 20 wt. % is maintained in the final alloy:

Copper between 1 wt. % and 10 wt. %, in lieu of an equal amount of nickel;

Niobium between 1 wt. % and 15 wt. %, in lieu of an equal amount of titanium;

Hafnium between 0.5 wt. % and 50 wt. %, in lieu of an equal amount of titanium;

Zirconium between 0.5 wt. % and 35 wt. %, in lieu of an equal amount of titanium;

Cobalt between 0.1 wt. % and 5 wt. %, in lieu of an equal amount of titanium, nickel, or a combination of titanium and nickel;

Chromium between 0.1 wt. % and 1 wt. %, in lieu of an equal amount of titanium; and/or Iron between 0.1 wt. % and 10 wt. %, in lieu of an equal amount of titanium, nickel, or a combination of titanium and nickel.

Figure 1B:
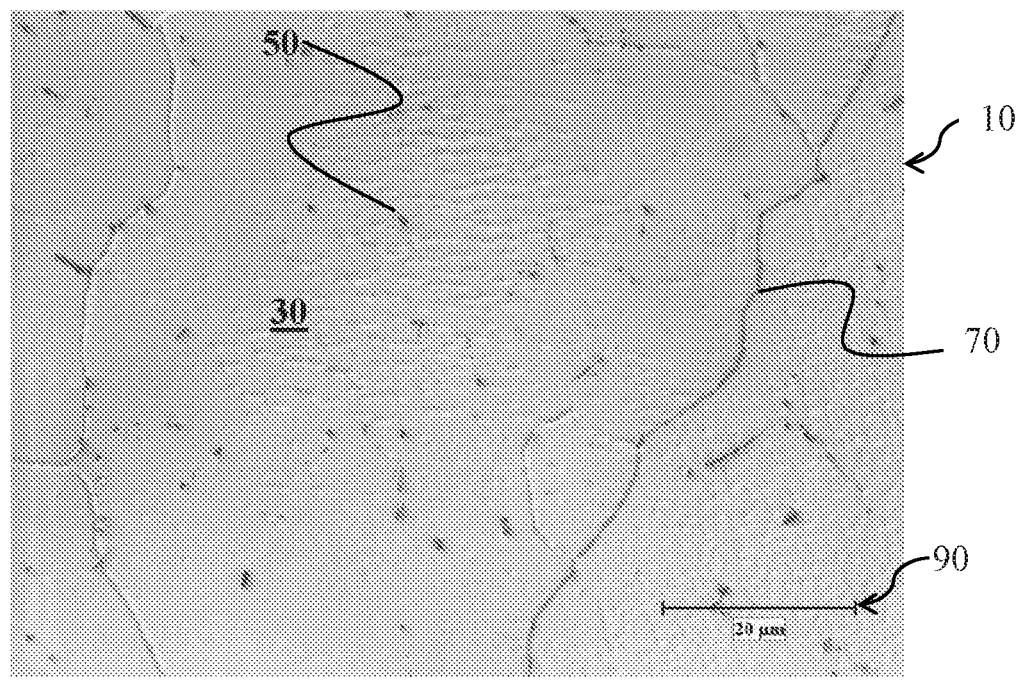
FIG. 1B is an image of an ingot of a NiTiY alloy made in accordance with the present disclosure with 0.04 wt. % yttrium in an as-cast condition, in which the ingot and its associated microstructural features are shown to scale according to the illustrated scale in micrometers in the bottom right hand corner of the figure.

Turning to FIG. 1B (which is drawn to scale, according to scale 90), a mictrostructure of an ingot 10 made of a NiTiY alloy in accordance with the present disclosure and having a yttrium concentration of 0.04 wt. % is shown in an as-cast condition at a magnification such that the scale 90 in the lower-right of the figure shows a length of 20 µm on the surface (or within the cross-section) of the ingot. As can be seen, the ingot 10 includes fine inclusions 50 present within the microstructure 30 of the alloy. Intact grain boundaries 70 are also shown. Inclusions 50 present in FIG. 1B are smaller in size and volume fraction as compared to those shown in FIG. 1A.

In particular, inclusions 50 are generally small relative to the resulting wire or other construct formed from ingot 10, even where the wire is a fine wire (e.g., wire 730 or 731 as shown in FIGS. 7A-7D and described in further detail below). In an exemplary embodiment, for example, inclusions 50 are no larger than 39 µm in any dimension in ingot 10 as defined in ASTM F2063, and are no larger than 10 µm in any dimension after ingot 10 has been processed into a hot-rolled coil according to ASTM F2063. In one particular exemplary embodiment, the transverse extent (i.e., measured perpendicular to the longitudinal axis of the wire) of inclusions 50 in cold-drawn wire is less than 2 µm such that inclusions 50 have a minimized effect on fatigue endurance of such a wire. In accordance with these exemplary embodiments, FIG. 1B illustrates that the addition of yttrium in the amount of 0.04 wt. % substantially eliminates the presence of large inclusions 5 (FIG. 1A) from the NiTiY alloy material, and instead includes only small NiTiY inclusions 50, e.g., having an average transverse dimension of about 1 µm. The small transverse dimension of inclusions 50 promotes enhanced fatigue life of the alloy 10, particularly when alloy 10 is processed into fine wire as discussed herein.

Figure 2A:
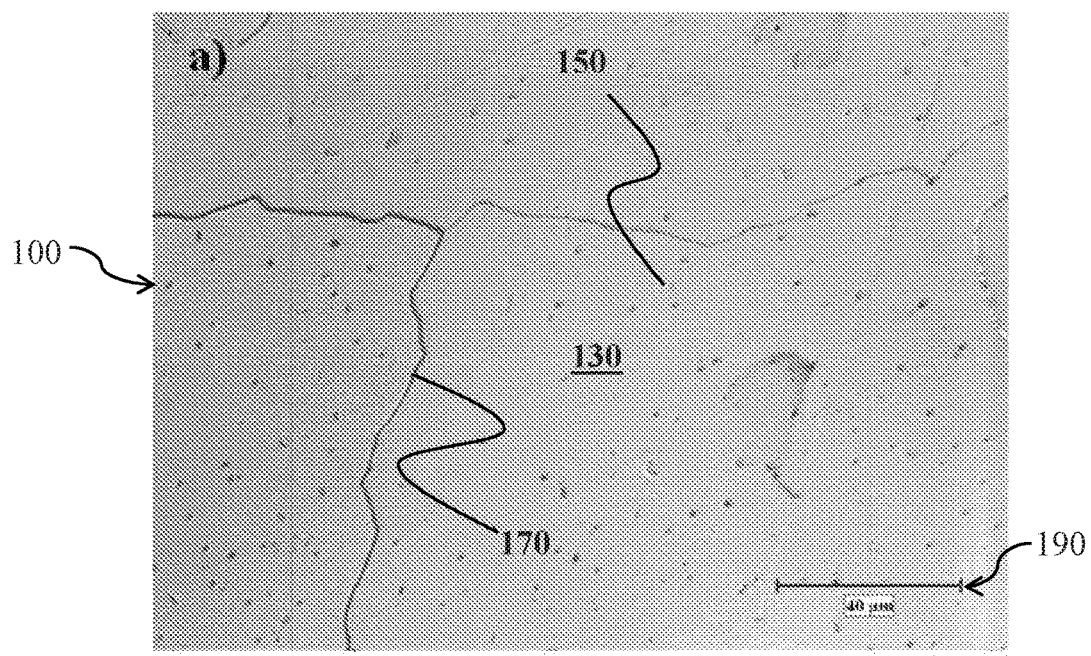
FIG. 2A is an image of an ingot of another NiTiY alloy made in accordance with the present disclosure with 0.01 wt. % yttrium in an as-cast condition, in which the ingot and its associated microstructural features are shown to scale according to the illustrated scale in micrometers in the bottom right hand corner of the figure.

Referring to FIG. 2A (which is drawn to scale, according to scale 190), the microstructure of an ingot 100 made of a NiTi alloy in accordance with the present disclosure and having a yttrium concentration of 0.01 wt. % is shown at a magnification such that the scale 190 in the lower-right of the figure shows a length of 40 µm on the surface (or within the cross-section) of the ingot. As can be seen, ingot 100 includes intact grain boundaries 170 and inclusions 150 present within the microstructure 130 of the alloy. As compared to those shown in FIG. 1A, inclusions 150 present in FIG. 2A are smaller and represent a lesser overall volume fraction of the parent material. In particular, inclusions 150 are substantially the same average transverse dimension as those of FIG. 1B. Inclusions 150 can therefore be expected to have a minimized effect on the fatigue endurance of the alloy due to their acceptably small sizes and extents, particularly when alloy 100 is processed into fine wire as discussed herein.

Figure 2B:
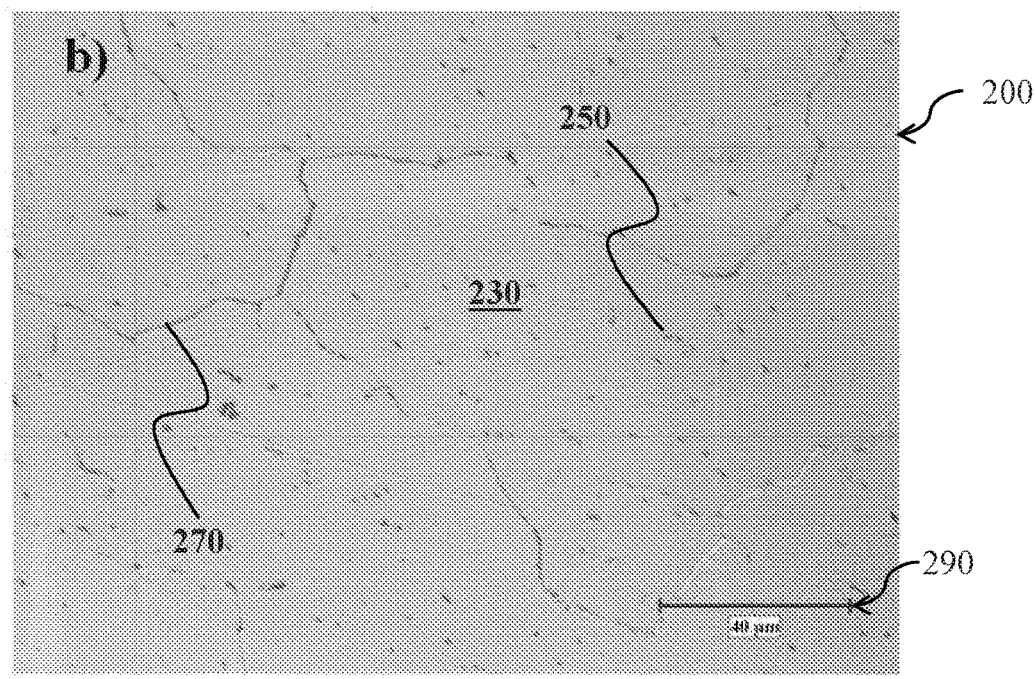
FIG. 2B is an image of an ingot of another NiTiY alloy made in accordance with the present disclosure with 0.02 wt. % yttrium in an as-cast condition, in which the ingot and its associated microstructural features are shown to scale according to the illustrated scale in micrometers in the bottom right hand corner of the figure.

Turning to FIG. 2B (which is drawn to scale, according to scale 290), the microstructure of an ingot 200 made of a NiTiY alloy in accordance with the present disclosure having a yttrium concentration of 0.02 wt. % at a magnification such that the scale 290 in the lower-right of the figure shows a length of 40 μm on the surface (or within the cross-section) of the ingot. As can be seen, ingot 200 has intact grain boundaries 270 and fine inclusions 250 present within the microstructure 230 of the alloy. Inclusions 250 are controlled in terms of size and volume fraction as compared to those shown in FIG. 1A. In particular, inclusions 250 are of substantially the same average transverse dimension as those of FIGS. 1A and 1B. Inclusions 250 can therefore be expected to have a minimized effect on the fatigue endurance of the alloy due to their acceptably small sizes and extents, particularly when alloy 10 is processed into fine wire as discussed herein.

Figure 2C:
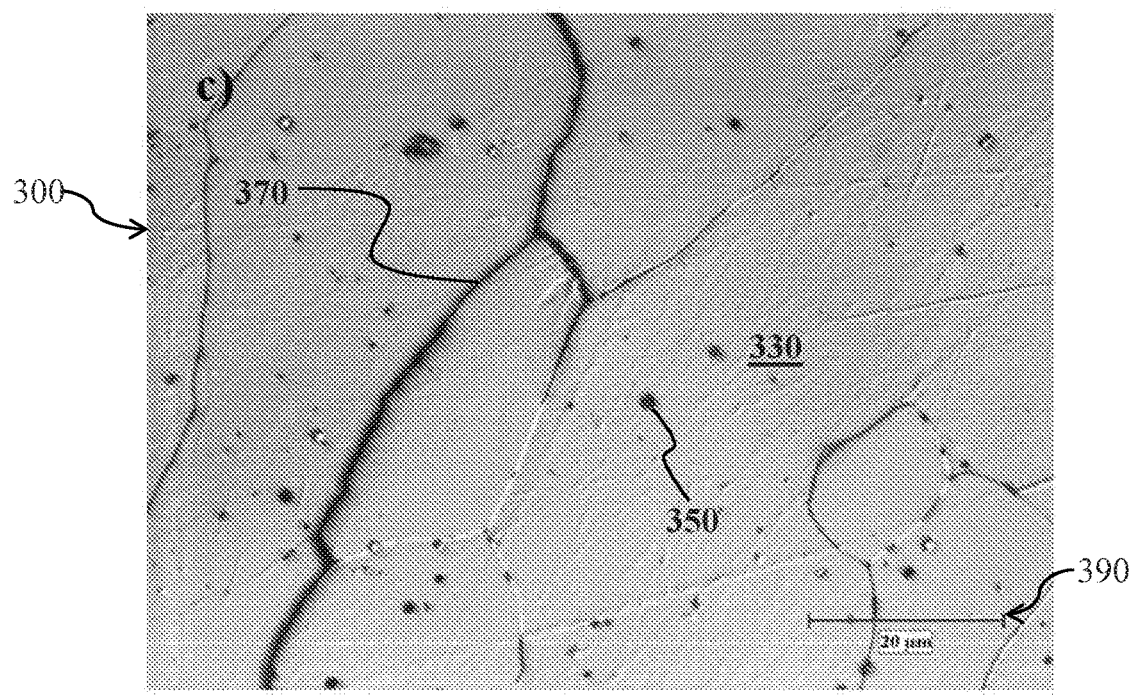
FIG. 2C is an image of an ingot of another NiTiY alloy made in accordance with the present disclosure with 0.16 wt. % yttrium in an as-cast condition, in which the ingot and its associated microstructural features are shown to scale according to the illustrated scale in micrometers in the bottom right hand corner of the figure.

Referring now to FIG. 2C (which is drawn to scale, according to scale 390), the microstructure of an ingot 300 made of a NiTiY alloy in accordance with the present disclosure having a yttrium concentration of 0.16 wt % is shown at a magnification such that the scale 390 in the lower-right of the figure shows a length of 20 μm on the surface (or within the cross-section) of the ingot. As can be seen, ingot 300 has inclusions 350 present within the microstructure 330 of the alloy. As compared to inclusions 5 of ingot 1 shown in FIG. 1A, inclusions 350 are smaller and represent a reduced volume fraction of the material. In particular, inclusions 350 are of substantially the same average transverse dimension and shape as the inclusions of FIGS. 1B, 2A, and 2B such that inclusions 350 can be expected to have a minimized effect on fatigue performance of the material of ingot 300.

However, cracks 370 are also present along some of the grain boundaries within the microstructure 330 of the alloy of FIG. 2C. Cracks 370 prevent ingot 300 from being worked into fine forms, e.g. fine wire 730, 731 described below. In particular, attempts to work ingot 300 into such fine forms results in propagation of cracks 370 and/or material failure stemming from cracks 370.

Figure 2D:
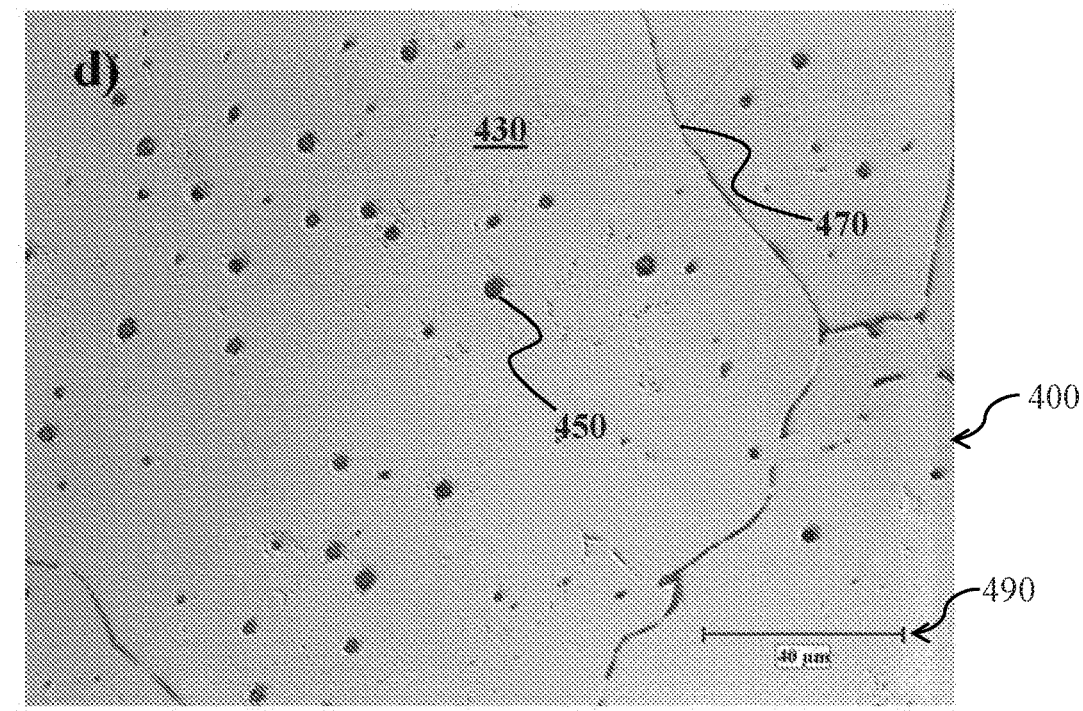
FIG. 2D is an image of an ingot of another NiTiY alloy made in accordance with the present disclosure with 0.3 wt. % yttrium in an as-cast condition, in which the ingot and its associated microstructural features are shown to scale according to the illustrated scale in micrometers in the bottom right hand corner of the figure.

Turning now to FIG. 2D (which is drawn to scale, according to scale 490), the microstructure of an ingot 400 made of a NiTiY alloy in accordance with the present disclosure having a yttrium concentration of 0.30 wt. % is shown at a magnification such that the scale 490 in the lower-right of the figure shows a length of 40 μm on the surface (or within the cross-section) of the ingot. As can be seen in FIG. 2D, ingot 400 has inclusions 450 present within the microstructure 430 of the alloy. Inclusions 450 have substantially the same average transverse dimension and shape as the inclusions of FIGS. 1B, 2A, and 2B, such that inclusions 450 can be expected to have a minimized effect on fatigue performance of the material ingot 400.

However, cracks 470 are also present along some of the grain boundaries within the microstructure 430 of the alloy. Cracks 470, similar to cracks 370 shown in FIG. 2C, prevent ingot 400 from being worked into fine forms, e.g. fine wire 730, 731 described below, without propagation or cracks 470 and/or material failure stemming from cracks 470.

By the foregoing findings, the inventors have determined that maintaining the yttrium concentration in a NiTiY alloy within a range of 0.01 wt. % to less than 0.16 wt. % (e.g., 0.15 wt. % or lower) provides a reduced average transverse inclusion dimension and a corresponding reduction in overall volume fractions of particles/inclusions, as shown in FIGS. 2A-2C. This beneficial result is achieved while also deterring cracking and minimizing brittleness of the material, thereby preserving the overall ductility and workability of the resulting alloy ingot.

Conversely, when the yttrium concentration in the NiTiY alloy rises to 0.16 wt. % and above, the as-casted ingot becomes too brittle and develops cracks, negating any potential for working into fine forms such as wire having a diameter less than 1 mm. In particular, NiTiY with greater than 0.16 wt. % yttrium develops cracks 370, 470 as shown in FIGS. 2C and 2D which preclude the use of cold work methods. Although these high yttrium concentrations do result in a reduction in average transverse inclusion dimension and volume fraction as compared to a binary NiTi alloy, the overall usefulness of the resulting alloy has been found to be impaired by its brittleness.

As noted above, yttrium can also be utilized with other NiTi based shape memory alloy systems to gain similar benefits to the ternary NiTiY alloys described above. Exemplary quaternary and quinary materials amenable to the beneficial addition of small amounts (e.g., up to 0.15 wt. %) of yttrium include Ni—Ti—Hf—Zr, Ni—Ti—Cr—Co—C, Ni—Ti—Fe—Co, Ni—Ti—Nb, Ni—Ti—Zr, Ni—Ti—Co, Ni—Ti—Cr, and Ni—Ti—Cu.

Figure 3A:
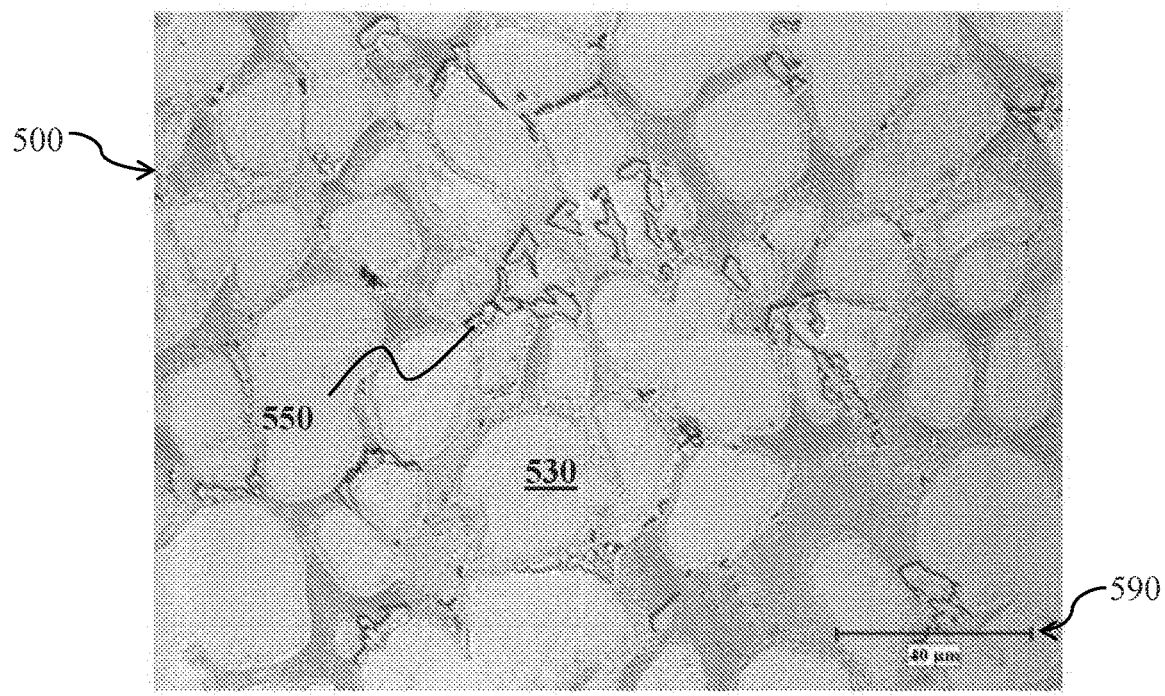
FIG. 3A is an image of an ingot of a NiTiNb alloy in an as-cast condition, in which the ingot and its associated microstructural features are shown to scale according to the illustrated scale in micrometers in the bottom right hand corner of the figure.
Figure 3B:
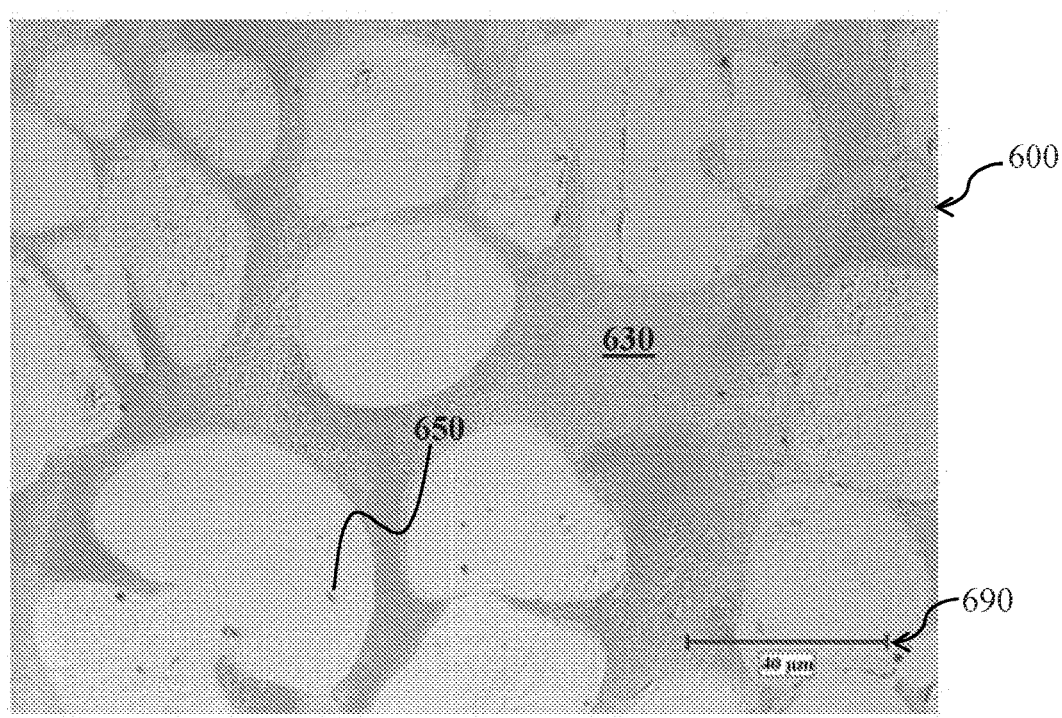
FIG. 3B is an image of a microstructure of a NiTiNb alloy made in accordance with the present disclosure, with 0.1 wt. % yttrium in an as-cast condition, in which the ingot and its associated microstructural features are shown to scale according to the illustrated scale in micrometers in the bottom right hand corner of the figure.

For example, a comparison of FIGS. 3A and 3B illustrates that a NiTiNb alloy can benefit from the use of yttrium in a similar fashion to binary NiTi as described in detail above. FIG. 3A (which is drawn to scale, according to scale 590), illustrates the microstructure of a control ingot 500 made of a NiTiNb alloy lacking yttrium. The image of FIG. 3A is shown at a magnification such that the scale 590 in the lower-right corner of the figure shows a length of 40 μm on the surface (or within the cross-section) of the ingot. As illustrated, ingot 500 includes inclusions 550 within the microstructure 530 of the alloy. Inclusions 550 are analogous to inclusions 5 of ingot 1 in that they may be responsible for large variations in fatigue life of the alloys.

Turning to FIG. 3B (which is drawn to scale, according to scale 690), the microstructure of a NiTiNbY ingot 600 made in accordance with the present disclosure is illustrated, in which the ingot 600 has a yttrium concentration of 0.1 wt. %. The image of FIG. 3B is shown at a magnification such that the scale 690 in the lower-right of the figure shows a length of 40 μm on the surface (or within the cross-section) of the ingot. As can be seen, ingot 600 has inclusions 650 present within the microstructure 630 of the alloy.

Similar to inclusions 50 of the ternary NiTiY alloy shown FIG. 1B, inclusions 650 of the present quaternary NiTiNbY alloy have a generally small size, with an average transverse inclusion dimension substantially smaller than inclusions 550 in control ingot 500. Inclusions 650 are small enough in the transverse direction to have a minimized effect on fatigue endurance of the material of ingot 600, even if such material is drawn to a fine wire as described further below. In addition, few or no cracks are evident within the microstructure 630 of ingot 600. Thus, the inventors have found that by adding a small amount of Y, such as 0.1 wt. % Y, to a nominally 47 wt. % Ni, 37 wt. % Ti, and 16 wt. % Nb alloy, the Ti oxide inclusions in the yttrium-free alloy (shown in FIG. 3A) can be substantially eliminated from cast ingots and other parts.

Wire Constructs Including NiTiY

Figure 6:
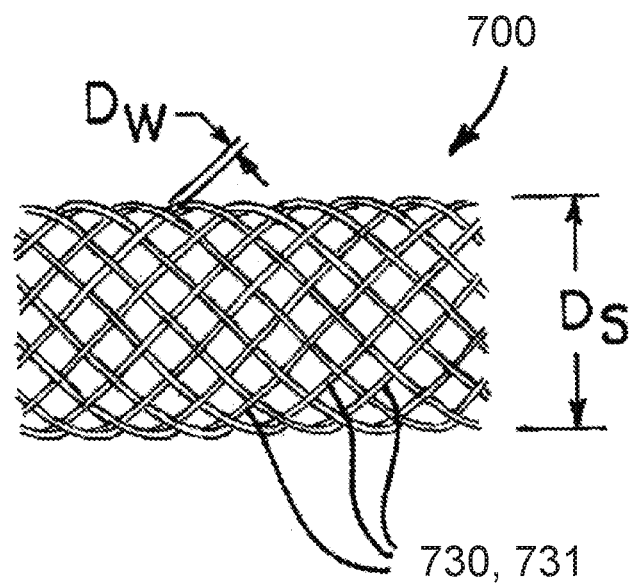
FIG. 6 is an elevation view illustrating the geometry of a braided stent having diameter $D_S$, the stent comprising wire elements formed into a mesh tubular scaffold, in accordance with the present disclosure.

In one exemplary embodiment, NiTiY material made in accordance with the present disclosure may be formed into a fine medical-grade wire 730, 731, as shown in FIG. 6. This wire 730, 731 may then be formed or integrated into a medical device, such as by braiding into a stent 700 having an overall device diameter $D_S$. Wires 730, 731 may each have an outer wire diameter $D_W$ of less than, e.g., 1 mm.

An alloy in accordance with the present disclosure may first be formed in bulk, such as by traditional casting methods. This bulk material is then formed into a suitable pre-form material (e.g., a rod, plate or hollow tube) by hot-working the bulk material into the desired pre-form size and shape. For purposes of the present disclosure, hot working is accomplished by heating the material to an elevated temperature above room temperature and performing desired shaping and forming operations while the material is maintained at the elevated temperature. The resulting pre-form material, such an ingot, is then further processed into an intermediate form, such as a rod, wire, tube, sheet or plate product by repetitive cold-forming and annealing cycles.

This intermediate material may be made by, for example, a schedule of drawing and annealing to create an initial coarse wire structure ready for final processing. Thereafter, wires 730 or 731 (FIGS. 6 and 7A-7D) may be subjected to a final cold work conditioning step, and possibly a final heat treatment step, in order to impart desired mechanical properties to the finished wire product as further described below.

Figure 7A:
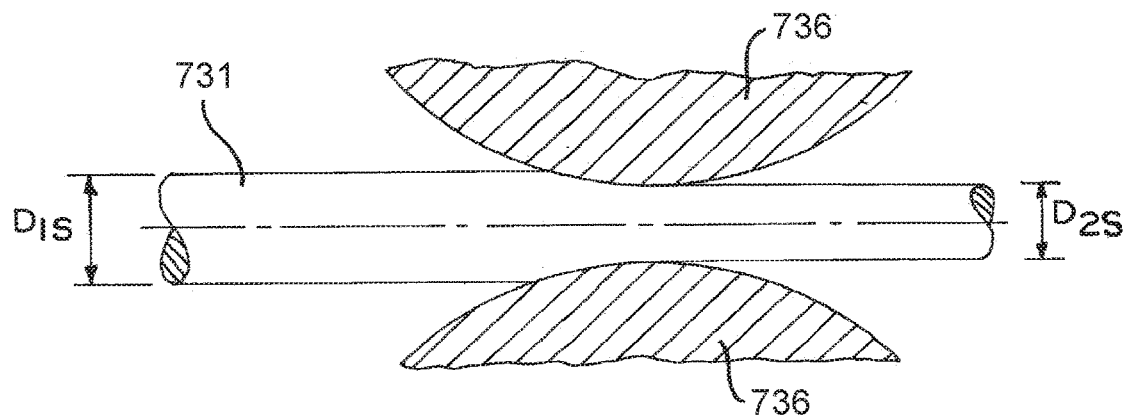
FIG. 7A is a schematic view illustrating an exemplary forming process of monolithic wire using a lubricated drawing die.

In one exemplary embodiment shown in FIG. 7A, monolithic wire 731 made of a NiTiY material (including ternary NiTiY as well as other alloys thereof) may be initially produced using conventional methods, including a schedule of drawing and annealing in order to convert the pre-form material (such as an ingot or rod) into a wire of a desired diameter prior to final processing. That is, the pre-form material is drawn through a die 736 (FIG. 7A) to reduce the outer diameter of the intermediate material slightly while also elongating the material, after which the material is annealed to relieve the internal stresses (i.e., retained cold work) imparted to the material by the drawing process. This annealed material is then drawn through a new die 736 with a smaller finish diameter to further reduce the diameter of the material, and to further elongate the material. Further annealing and drawing of the material is iteratively repeated until the material is formed into a wire construct ready for final processing into wire 731.

Figure 7B:
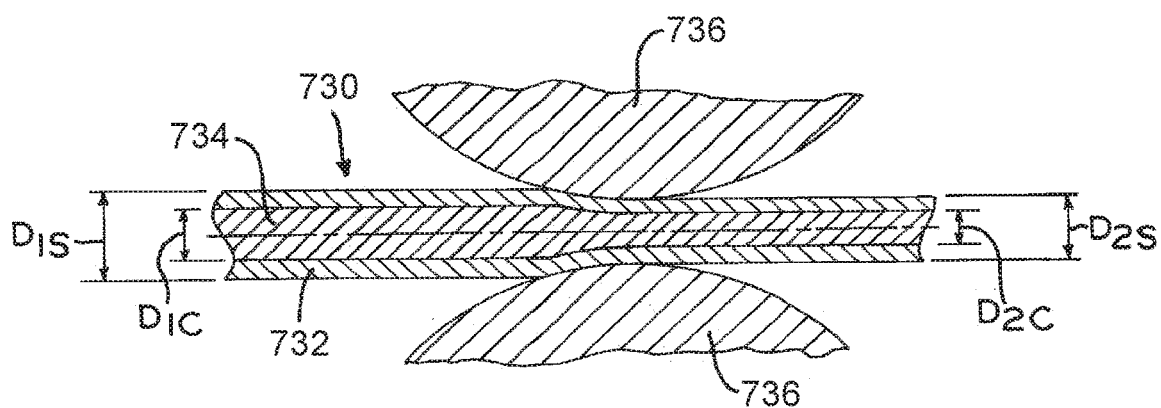
FIG. 7B is a schematic view illustrating an exemplary forming process of composite wire using a lubricated drawing die.

To form composite wire 730 (FIG. 7B) such as DFT®, core 734 is inserted within shell 732 to form an intermediate construct, and an end of this intermediate construct is then tapered to facilitate placement of the end into a drawing die 736 (FIG. 7B). The end protruding through the drawing die 736 is then gripped and pulled through the die 736 to reduce the diameter of the construct and bring the inner surface of shell 732 into firm physical contact with the outer surface of core 734. More particularly, the initial drawing process reduces the inner diameter of shell 732, such that shell 732 closes upon the outer diameter of core 734 and the inner diameter of shell 732 equals the outer diameter of core 734 whereby, when viewed in section, the inner core 734 will completely fill the outer shell 732 as shown in FIG. 7B.

Exemplary composite wires 730 may be formed using a NiTiY alloy made in accordance with the present disclosure (including ternary NiTiY as well as other alloys thereof) for shell 732 and either platinum (Pt) or tantalum (Ta) for core 734. Addition of such materials contributes to the radio-opacity, or visibility under x-ray, of nitinol in fine wire form.

The step of drawing subjects wire 730 or 731 to cold work. For purposes of the present disclosure, cold-working methods effect material deformation at or near room temperature, e.g. 20-30° C. In the case of composite wire 730, drawing imparts cold work to the material of both shell 732 and core 734, with concomitant reduction in the cross-sectional area of both materials. The total cold work imparted to wire 730 or 731 during a drawing step can be characterized by the following formula (I):

$$cw = 1 - \left(\frac{D_2}{D_1}\right)^2 \times 100\% \quad \text{(I)}$$

wherein "cw" is cold work defined by reduction of the original material area, "$D_{2S}$" is the outer cross-sectional diameter of the wire after the draw or draws, and "$D_{1S}$" is the outer cross-sectional diameter of the wire prior to the same draw or draws.

Referring to FIGS. 7A and 7B, the cold work step may be performed by the illustrated drawing process. As shown, wire 730 or 731 is drawn through a lubricated die 736 having an output diameter $D_{2S}$, which is less than diameter $D_{1S}$ of wire 730 or 731 prior to the drawing step. The outer diameter of wire 730 or 731 is accordingly reduced from pre-drawing diameter $D_{1S}$ to drawn diameter $D_{2S}$, thereby imparting cold work cw.

Alternatively, net cold work may be accumulated in wire 730 or 731 by other processes such as cold-swaging, rolling the wire (e.g., into a flat ribbon or into other shapes), extrusion, bending, flowforming, or pilgering. Cold work may also be imparted by any combination of techniques including the techniques described here, for example, cold-swaging followed by drawing through a lubricated die finished by cold rolling into a ribbon or sheet form or other shaped wire forms. In one exemplary embodiment, the cold work step by which the diameter of wire 730 is reduced from $D_{1S}$ to $D_{2S}$ is performed in a single draw and, in another embodiment, the cold work step by which the diameter of wire 730 is reduced from $D_{1S}$ to $D_{2S}$ is performed in multiple draws which are performed sequentially without any annealing step therebetween. When calculating cold work cw using formula (I) above, it is assumed that no anneal has been performed subsequent to the process of imparting cold work to the material.

For processes where the drawing process is repeated without an intervening anneal on composite wire 730, each subsequent drawing step further reduces the cross section of wire 730 proportionately, such that the ratio of the sectional area of shell 732 and core 734 to the overall sectional area of wire 730 is nominally preserved as the overall sectional area of wire 730 is reduced. Referring to FIG. 7B, the ratio of pre-drawing core outer diameter $D_{1C}$ to pre-drawings shell outer diameter $D_{is}$ is the same as the corresponding ratio post-drawing. Stated another way, $D_{1C}/D_{1S}=D_{2C}/D_{2S}$.

Thermal stress relieving, otherwise known in the art as annealing, at a nominal temperature not exceeding the melting point of the wire material (or, for a composite wire, either the first or second materials), is used to improve the ductility of the fully dense composite between drawing steps, thereby allowing further plastic deformation by subsequent drawing steps. Further details regarding wire drawing are discussed in U.S. Pat. No. 7,989,703, issued Aug. 2, 2011, entitled "Alternating Core Composite Wire", assigned to the assignee of the present invention, the entire disclosure of which is incorporated by reference herein.

Heating wire 730 to a temperature sufficient to cause recrystallization of grains eliminates accumulated cold work. The cold work imparted by each iterative cold work process is relieved by fully annealing the material between draws, thereby enabling the next iterative cold working process. In full annealing, the cold-worked material is heated to a temperature sufficient to substantially fully relieve the internal stresses stored in the material, thereby relieving the stored cold work and "resetting" cold work to zero.

Figure 7C:
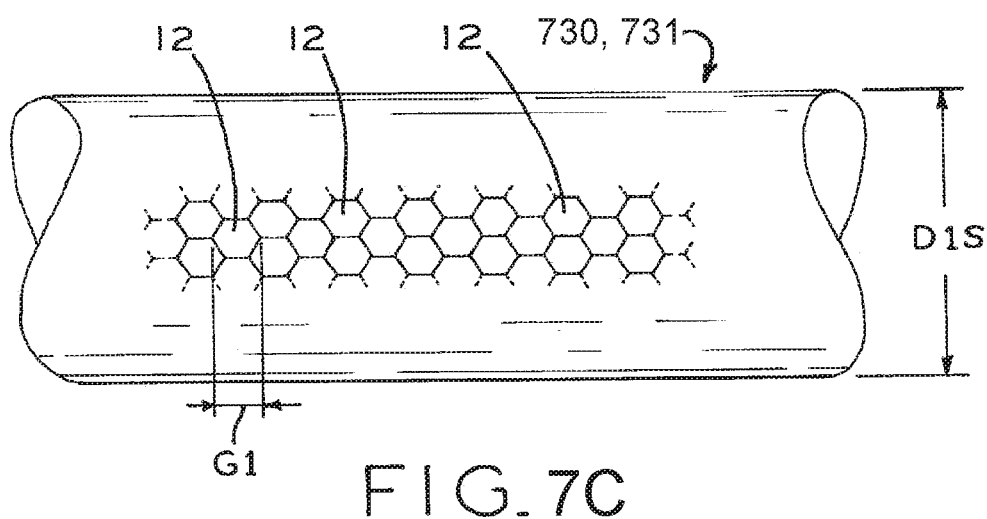
FIG. 7C is an elevation view of a wire in accordance with the present disclosure, before a final cold working process.
Figure 7D:
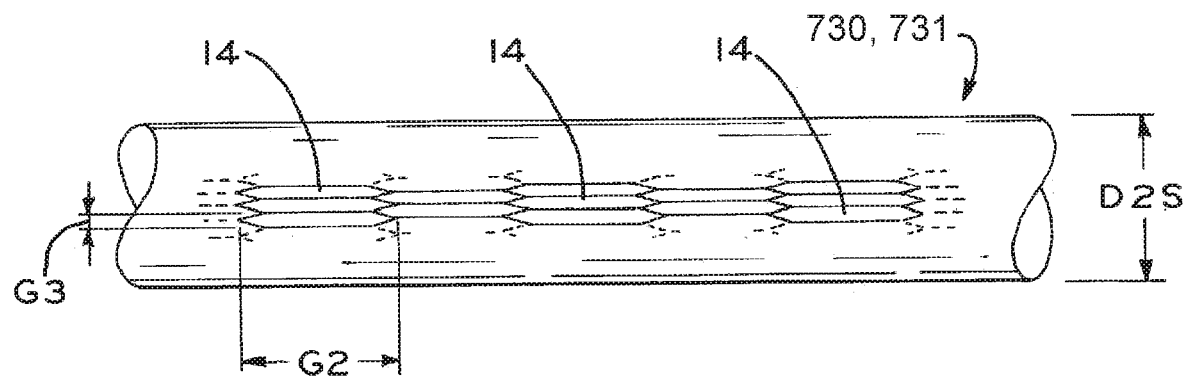
FIG. 7D is an elevation view of the wire of FIG. 7C, after the final cold working process.

On the other hand, wires 730 or 731 subject to drawing or other mechanical processing without a subsequent annealing process retain an amount of cold work. The amount of retained work depends upon the overall reduction in diameter from $D_{1S}$ to $D_{2S}$, and may be quantified on the basis of individual grain deformation within the material as a result of the cold work imparted. Referring to FIG. 7C, for example, wire 731 is shown in a post-annealing state, with grains 12 shown substantially equiaxed, i.e., grains 12 define generally spheroid shapes in which a measurement of the overall length G1 of grain 12 is substantially the same regardless of the direction of measurement. After drawing wire 731 (as described above), equiaxed grains 12 are converted into elongated grains 14 (FIG. 7D), such that grains 14 are longitudinal structures defining an elongated grain length G2 (i.e., the longest dimension defined by grain 14) and a grain width G3 (i.e., the shortest dimension defined by grain 14). The elongation of grains 14 results from the cold working process, with the longitudinal axis of grains 14 generally aligned with the direction of drawing, as illustrated in FIG. 7D.

The retained cold work of wire 731 after drawing can be expressed as the ratio of the elongated grain length G2 to the width G3, such that a larger ratio implies a grain which has been "stretched" farther and therefore implies a greater amount of retained cold work. By contrast, annealing wire 731 after an intermediate drawing process recrystallizes the material, converting elongated grains 14 back to equiaxed grains 12 and "resetting" the retained cold work ratio to 1:1 (i.e., no retained cold work).

For the present NiTiY materials, full annealing may be accomplished at a temperature about 500-800° C. for at least several seconds for thin wire (i.e., having a small cross-sectional area of between 0.000127 sq. mm and 0.5 sq. mm) to tens of minutes for thicker materials (i.e., having a larger cross-sectional area of between 1 sq. mm and 125 sq. mm). Alternatively, a full anneal can be accomplished with a higher temperature, such as between 700° C. and 1100° C., for a shorter time, such as between several milliseconds and less than 5 minutes, again depending on cross-sectional area of the material. Of course, a relatively higher temperature annealing process can utilize a relatively shorter time to achieve a full anneal, while a relatively lower temperature will typically utilize a relatively longer time to achieve a full anneal. In addition, annealing parameters can be expected to vary for varying wire diameters, with smaller diameters shortening the time of anneal for a given temperature. Whether a full anneal has been accomplished can be verified in a number of ways as well known in the art, such as microstructural examinations using scanning electron microscopy (SEM), mechanical testing for ductility, strength, elasticity, etc., and other methods.

Further discussion of cold working and annealing methods can be found in U.S. Pat. No. 8,840,735, issued Sep. 23, 2014 and entitled FATIGUE DAMAGE RESISTANT WIRE AND METHOD OF PRODUCTION THEREOF, the entire disclosure of which is hereby incorporated by reference.

The resulting coarse wire material may then be finally processed into a final form, such as a fine wire suitable for integration into a stent or other medical device. Exemplary wire constructs are described in further detail below.

Wire Properties

Fatigue endurance of the present NiTiY alloys can be enhanced depending on the concentration of yttrium added to the alloy, as described in detail above. For example, as found in Example 1 below, a NiTiY wire can exhibit a "runout" fatigue life of $10^7$ cycles at a strain amplitude of 0.1% in the absence of controllable external factors (e.g., imperfections in drawing dies leading to microstructural defects, or other production irregularities). For purposes of the present disclosure, "runout" fatigue is a number of fatigue cycles beyond which the subject material is not expected to experience fatigue failure at any number of additional cycles.

This enhanced fatigue endurance of the present NiTiY wire materials enables the alloy to be used in in vivo applications such as stents, including vascular (e.g., cardiac) and non-vascular (e.g., gastrointestinal, urinary) stents. Because alloys used in stents and similar in vivo applications may undergo many cycles, the present wire is ideally suited for use in stents implanted in high-flexion areas (i.e., extremities) and other demanding applications.

Material properties of the present NiTiY wire materials other than fatigue resistance are commensurate with similar binary NiTi materials. The present NiTiY materials are therefore suitable for medical device applications where NiTi is currently used, such as stents, pacing leads, etc.

EXAMPLES

The following non-limiting Examples illustrate various features and characteristics of the present invention, which is not to be construed as limited thereto.

In these Examples, exemplary monolithic NiTiY alloy wires in accordance with the present disclosure were produced, tested and characterized, particularly with regard to material workability and mechanical strength.

Mechanical performance was then evaluated for each cold worked sample via a uniaxial tensile test on an Instron Model 5565 test machine available from Instron or Norwood, Mass., USA). More specifically, destructive uniaxial tension testing of the wire materials was used to quantify the ultimate strength, yield strength, axial stiffness and ductility of candidate materials, using methods described in *Structure-Property Relationships in Conventional and Nanocrystalline NiTi Intermetallic Alloy Wire, Journal of Materials Engineering and Performance* 18, 582-587 (2009) by Jeremy E. Schaffer, the entire disclosure of which is hereby expressly incorporated herein by reference. These tests are run using servo-controlled Instron load frames in accordance with industry standards for the tension testing of metallic materials.

For rotary beam fatigue testing in accordance with the Examples herein, a wire sample is cut to a length of approximately about 118 mm (e.g., for a 0.33 mm diameter wire), then secured at its axial ends to rotatable jaws. The free portion of the wire between the jaws is bent to introduce a desired tensile strain at the "peak" or outermost portion of the bend. Directly opposite this peak of the bend, the wire experiences a compressive strain equal to the tensile strain, with the nominal value of both the tensile and compressive strains referred to herein as the "strain amplitude." The jaws are then rotated in concert (i.e., each jaw rotated with the same speed and in the same direction), such that the area of maximum tensile strain is rotated around the wire "peak" and transitioned to the area of maximum compressive strain with each 180-degree rotation of the jaws and wire. Rotary beam fatigue testing is further described in ASTM E2948-14, the entire disclosure of which is hereby expressly incorporated herein by reference.

Example 1

Figure 4:
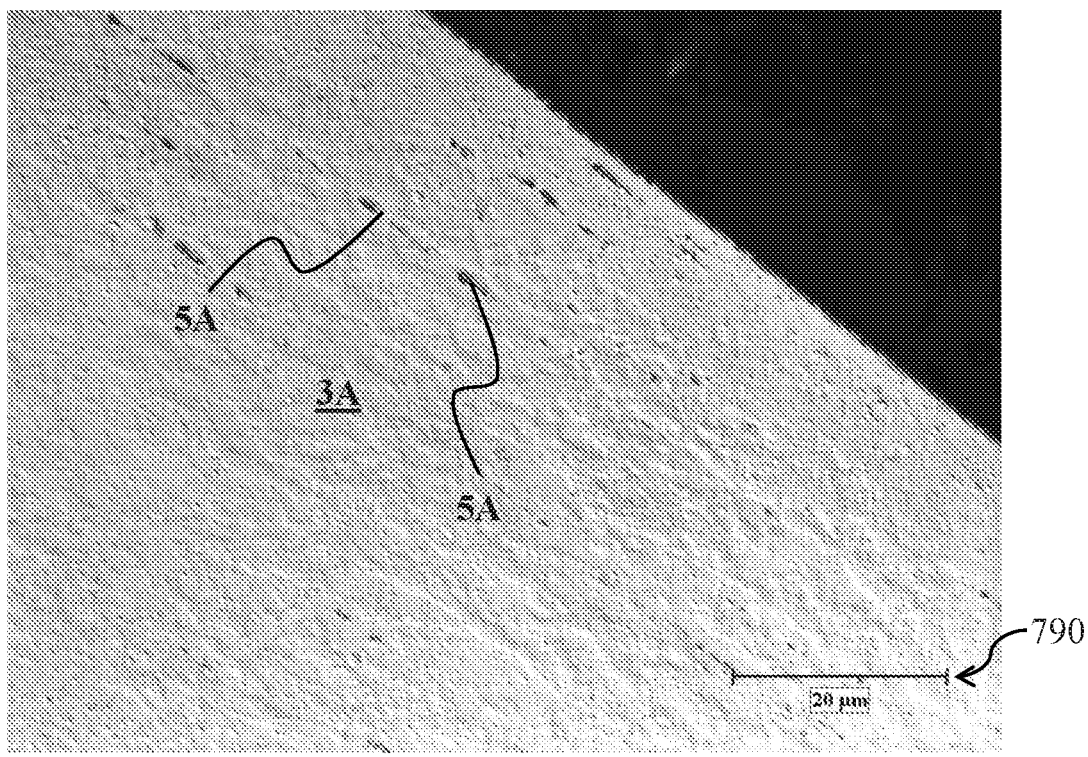
FIG. 4 is an image of a portion of a longitudinal cross section of the NiTiY alloy of FIG. 2B, in which the features of the wire are shown to scale according to the illustrated scale in micrometers in the bottom right hand corner of the figure.

A NiTiY alloy with low Y content was vacuum induction melted and cast into an ingot in the form of a rod having a 2-inch diameter, the microstructure of which is shown in FIG. 2B. The NiTiY alloy was made in accordance with the present disclosure and has concentrations of 56.78 wt. % Ni, 43.06 wt. % Ti, 0.02 wt. % Y, 0.03 wt. % O, with the balance being incidental impurities. The alloy was homogenized at 1000° C. for 72 hours and then hot worked to a 0.144 inch diameter rod. It was then cold drawn through standard wire-drawing practices, as described above, to a diameter of 0.0128 inches and annealed at 500° C. for 5 minutes to achieve a super-elastic property. As shown in FIG. 4 (which is drawn to scale, according to scale 790) microstructural analysis of the resulting alloy 3A showed that inclusions 5A had an average transverse dimension of less than 1 μm.

Figure 5:
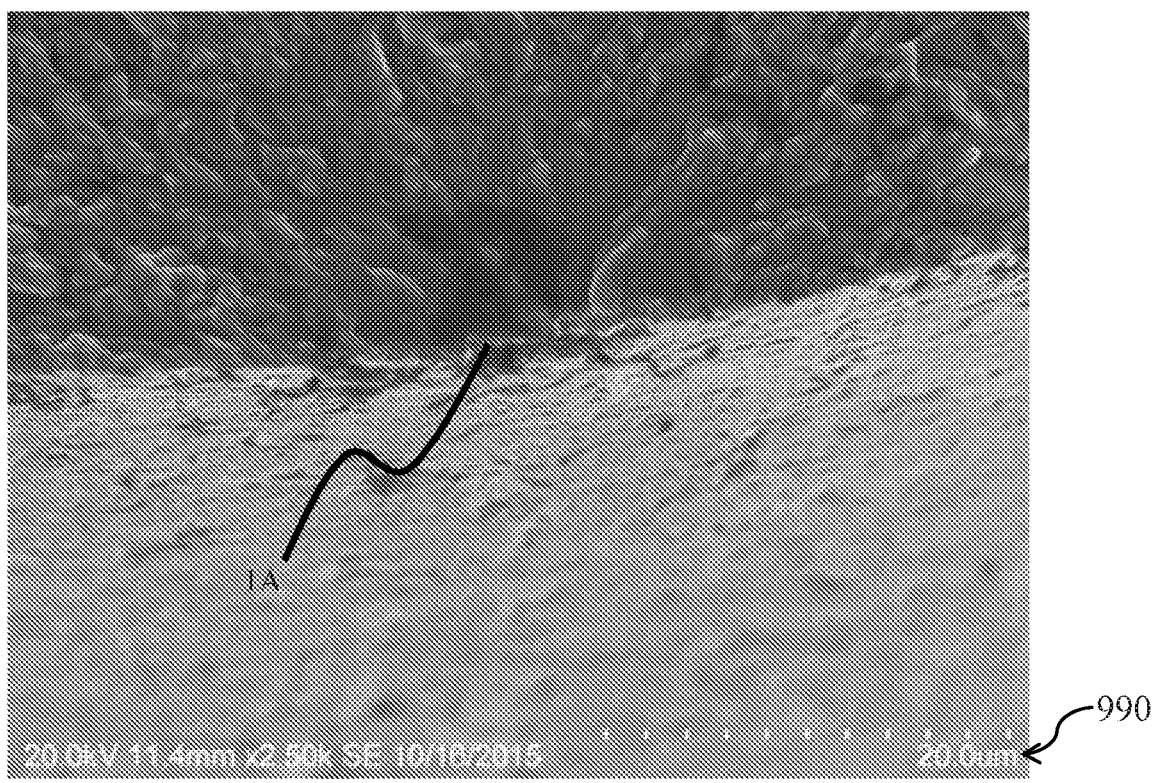
FIG. 5 is an image showing a fracture face after fatigue testing for 2,996,258 cycles in a sample of the NiTiY alloy of FIG. 4, in which the features of the wire are shown to scale according to the illustrated scale in micrometers in the bottom right hand corner of the figure.

Rotary beam fatigue testing was carried out on the super-elastic wire sample. Thirteen samples of the alloy were tested, and the tests were conducted at a strain amplitude of 1% and a rotation frequency of 60 Hz. The wire was kept in a bath of purified (via reverse osmosis) water at 37° C. and left to cycle until the "runout" level of $10^7$ cycles was reached or the wire experienced failure, whichever occurred first. Twelve of the thirteen samples reached the "runout" level of $10^7$ cycles. One sample fractured at 2,996,258 cycles (see, e.g., fracture 1A in FIG. 5, which is drawn to scale according to scale 990).

The data developed for the alloy in the present Example compares favorably with standard (Y-free) NiTi (see Example 2), demonstrating that the present NiTiY material consistently outperforms binary NiTi in fatigue life.

Example 2

A standard binary NiTi alloy having concentrations of 56.23 wt. % Ni, 43.75 wt. % Ti, and incidental impurities wire was drawn to a 0.0128 inch diameter wire and annealed to achieve a super-elastic property.

Rotary beam fatigue testing was conducted. Ten samples of the alloy were tested, and the tests were conducted at a strain amplitude of 1% and a rotation frequency of 60 Hz. The wire was kept in a bath of purified (via reverse osmosis) water at 37° C. and left to cycle until the "runout" level of $10^7$ cycles was reached or the wire experienced failure, whichever occurred first. For the ten samples, the mean number of cycles to reach failure was 18,452 cycles, with a maximum of 21,805 cycles and a minimum of 14,936 cycles.

Accordingly, the binary NiTi wires exhibited inferior fatigue resistance as compared to the NiTiY wires made in accordance with the present disclosure.

Example 3

A NiTiY alloy with high Y content was vacuum induction melted and cast into an ingot in the form of a rod having a 2-inch diameter. The NiTiY alloy was made in accordance with the present disclosure and has concentrations of 56.74 wt. % Ni, 43.05 wt. % Ti, 0.16 wt. % Y, 0.03 wt. % O, with the balance being incidental impurities. The as-cast ingot, the microstructure of which is shown in FIG. 2C, was brittle, and cracks were apparent in the microstructure. The cracks precluded the alloy from being worked into a wire.

Accordingly, the NiTiY wires made with a low concentration of yttrium (i.e., no more than 0.15 wt. %) exhibited superior workability as compared to the higher-concentration (i.e., 0.16 wt. %) samples.

While this invention has been described as having an exemplary design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of making a nickel-titanium (NiTi) alloy consisting of nickel, titanium and yttrium with inevitable impurities, the method comprising:
   providing between 50 wt. % nickel and 60 wt. % nickel;
   providing between 40 wt. % titanium and 50 wt. % titanium, the titanium having a purity of up to about 99.8%;
   providing between 0.01 wt. % yttrium and 0.15 wt. % yttrium; and
   vacuum melting the components under a vacuum pressure of about 0.67 Pa to form an ingot including the nickel, the titanium and the yttrium;
   forming the ingot into a fine wire construct having a diameter of up to 1 mm, the step of forming accomplished by repetitive hot or cold working and annealing cycles; and
   cold working and applying a heat treatment step to impart superelastic mechanical properties;
   wherein the fine wire product has a fatigue endurance such that the wire product survives 1 million cycles at a strain amplitude of 1%.

2. The method of claim 1, further comprising forming the ingot into an intermediate construct comprising one of a rod, wire, tube, sheet or plate by repetitive cold-forming and annealing cycles.

3. The method of claim 2, wherein the NiTi alloy has Ti-rich oxides with an average transverse inclusion dimension less than 2 μm.

4. The method of claim 3, wherein the NiTi alloy comprises one or more impurities of up to 0.05 wt. % each.

5. The method of claim 2, wherein the NiTi alloy has Ti-rich oxides with an average transverse inclusion dimension less than 1 μm.

6. The method of claim 5, wherein the NiTi alloy comprises one or more impurities of up to 0.05 wt. % each.

7. The method of claim 1, wherein the NiTi alloy has Ti-rich oxides with an average transverse inclusion dimension less than 2 μm.

8. The method of claim 7, further comprising forming the ingot into an intermediate construct comprising one of a rod, wire, tube, sheet or plate by repetitive cold-forming and annealing cycles.

9. The method of claim 8, wherein the NiTi alloy comprises one or more impurities of up to 0.05 wt. % each.

10. The method of claim 7, wherein the NiTi alloy comprises one or more impurities of up to 0.05 wt. % each.

11. The method of claim 1, wherein the NiTi alloy has Ti-rich oxides with an average transverse inclusion dimension less than 1 μm.

12. The method of claim 11, further comprising forming the ingot into an intermediate construct comprising one of a rod, wire, tube, sheet or plate by repetitive cold-forming and annealing cycles.

13. The method of claim 12, wherein the NiTi alloy comprises one or more impurities of up to 0.05 wt. % each.

14. The method of claim 11, wherein the NiTi alloy comprises one or more impurities of up to 0.05 wt. % each.

15. The method of claim 1, wherein the NiTi alloy comprises one or more impurities of up to 0.05 wt. % each.

* * * * *